United States Patent [19]

Konijnenberg et al.

[11] 4,119,782

[45] Oct. 10, 1978

[54] PROCESS FOR THE PREPARATION OF 5-(4-AMINOBUTYL) HYDANTOIN AND/OR 1-UREIDO-5-AMINOCAPRONAMIDE

[75] Inventors: Erik Konijnenberg, Nuth; Franciscus H. A. M. J. Vandenbooren, Maastricht; Egidius J. M. Verheijen, Born, all of Netherlands

[73] Assignee: Stamicarbon, B.V., Geleen, Netherlands

[21] Appl. No.: 784,368

[22] Filed: Apr. 4, 1977

[30] Foreign Application Priority Data

Apr. 9, 1976 [NL] Netherlands ............... 7603742

[51] Int. Cl.$^2$ ............... C07D 233/76; C07C 127/15
[52] U.S. Cl. ............... 548/313; 260/553 R
[58] Field of Search ............... 548/313; 260/553 R

[56] References Cited

U.S. PATENT DOCUMENTS

| | | | |
|---|---|---|---|
| 2,688,023 | 8/1954 | Rogers | 548/313 |
| 3,210,400 | 10/1965 | Brakebill | 548/313 |
| 3,758,494 | 9/1973 | Suverkropp et al. | 548/313 |
| 3,911,001 | 10/1975 | Suverkropp et al. | 548/313 |

FOREIGN PATENT DOCUMENTS

| | | | |
|---|---|---|---|
| 546,867 | 10/1957 | Canada | 548/313 |
| 1,358,202 | 3/1964 | France | 548/313 |
| 39-19,805 | 9/1964 | Japan | 548/313 |
| 39-19,806 | 9/1964 | Japan | 548/313 |

OTHER PUBLICATIONS

Chemical Abstracts Fifth Decennial Index, vols. 41–50, 1947–1956, Subjects TH–Z, p. 13169s.
Chemical Abstracts Subject Index, A–H, vol. 56, Jan.–Jun. 1962, pp. 26N–28N.

*Primary Examiner*—Natalie Trousof
*Attorney, Agent, or Firm*—Cushman, Darby & Cushman

[57] ABSTRACT

5-(4-Aminobutyl) hydantoin is prepared by hydrogenation of 5-(3-cyanopropyl) hydantoin in the liquid phase with a catalyst and ammonia in the presence of greater than 0.4 up to about 2.0 of a dissolved alkali hydroxide per mole of hydantoin to be hydrolyzed. Use of the stated quantity of alkali hydroxide avoids catalyst loss by dissolution yet maintains hydrogenation efficiency.

4 Claims, No Drawings

PROCESS FOR THE PREPARATION OF 5-(4-AMINOBUTYL) HYDANTOIN AND/OR 1-UREIDO-5-AMINOCAPRONAMIDE

BACKGROUND OF THE INVENTION

The present invention relates to the preparation of 5-(4-aminobutyl) hydantoin and/or 2-ureido-6-aminocapronamide by hydrogenating 5-(3-cyanopropyl) hydantoin and/or 2-ureido-5-cyano-valeramide in the liquid phase and in the presence of ammonia using a hydrogenation catalyst. The reaction product can be converted into lysine by hydrolysis according to known procedures.

This type of hydrogenation can be carried out with various hydrogenation catalysts, and gives high yields according to U.S. Pat. Nos. 3,758,494 and 3,911,001. In most cases according to these patents, nickel or cobalt is preferred as hydrogenation catalyst.

However, a closer study of this hydrogenation process has revealed that with nickel, cobalt or both being used as the catalyst, fairly large amounts of catalyst are lost owing to dissolution of the nickel or cobalt in the reaction medium.

DESCRIPTION OF THE INVENTION

We have now found that the amount of dissolved nickel or cobalt in the reaction medium can be appreciably diminished by dissolving in the reaction medium an amount of an alkali hydroxide greater than 0.4 mole per mole of the compound to be hydrogenated. On the other hand, we have also found that too much alkali hydroxide has an unfavorable effect on the selectivity of the reaction, but that a sufficiently high selectivity and yields can be maintained if not more than about 2 moles of alkali hydroxide are used per mole of compound to be hydrogenated.

Accordingly, the process according to the present invention for preparing 5-(4-aminobutyl) hydantoin and/or 2-ureido-6-aminocapronamide by hydrogenation of 5-(3-cyanopropyl) hydantoin and/or 2-ureido-5-cyanovaleramide in the liquid phase and in the presence of ammonia with a hydrogenation catalyst containing nickel and/or cobalt is, therefore, characterized in that the hydrogenation is conducted in the presence of more than 0.4 mole and not more than about 2 moles of dissolved alkali hydroxide per mole of the compound to be hydrogenated.

The presence of dissolved alkali hydroxide in the reaction mixture is conveniently realized by adding alkali hydroxide as such, however, the same effect can be achieved in situ by adding an alkali salt of a weak acid (e.g. the carbonates or bicarbonates of the alkali metals, esp. $Na_2CO_3$ or $NaHCO_3$) or an alkali oxide. The particular manner in which the prescribed concentration is arrived at is not critical so long as the reactants are not adversely effected.

In the process according to the present invention, various alkali hydroxides can be employed such as sodium hydroxide, potassium hydroxide and lithium hydroxide. Best results are obtained when about 0.6 to about 1.5 mole of alkali hydroxide are used per mole of compound to be hydrogenated, because under these conditions the tendency of the catalyst to go into solution can be very effectively suppressed without catalyst solution supressing having any adverse effects on the reactions.

The hydrogenation can very conveniently be carried out in a solvent at elevated temperature, such as between about 50° and 250° C., while the partial hydrogen pressure can be varied within wide limits, for instance, between 1 and 200 atmospheres. Suitable non-reactive solvents include water, methanol, ethanol, iso-propanol, butanols, glycols, dioxane, tetrahydrofuran and also other solvents or solvent mixtures which are inert under the reaction conditions. The solvent temperature and pressure conditions are all, to a certain extent, interrelated and one will select the appropriate set of parameters to optimize the reaction environment.

The amount of ammonia in the reaction medium may be varied, but normally an amount of about 10–30% wt. of $NH_3$, calculated on the total amount of reaction mixture, is employed. Further details regarding catalyst systems, reactants, pressure and temperature reaction conditions and ammonia concentration are found in U.S. Pat. Nos. 3,758,494 and 3,911,001, the disclosures of which are hereby incorporated by reference.

The following examples will serve to further illustrate our invention. Unless otherwise indicated, all parts and percentages are by weight. Comparative examples A-C are not according to the present invention.

EXAMPLE 1

Raney nickel (12.5g), ammonia (1500 ml, 25% wt) and sodium hydroxide (30g, a ratio of 1 mole per mole of hydantoin) are fed into an autoclave (5 liter) which is equipped with a stirrer, an inlet tube and a draining system, whereupon the autoclave is closed. Next, hydrogen is introduced to raise the pressure to 60 atm, and the temperature is slowly increased to 110° C. with simultaneous stirring. After this, a sample is taken for determination of the nickel content. The amount of nickel in this sample was found to be 3 mg per liter of catalyst suspension.

While this suspension in the autoclave is being stirred, a solution of 5-(3-cyanopropyl) hydantoin (125g) in ammonia (1500 ml, 25% wt) is added over a period of 20 minutes and stirring continued for 2 hours. Then, another sample is taken and the nickel content is again determined and found to be 7 mg of nickel per liter of reaction mixture. The amount of 5-(3-cyanopropyl) hydantoin in a portion of this sample was determined by means of ion exchange chromatography, cyano-hydantoin was no longer detected proving the degree of conversion to be 100%.

Another portion of the sample is hydrolyzed, whereupon the amount of lysine so formed is determined by ion-exchange chromatography. This test reveals that at least 87% of the cyano hydantoin has been converted into hydrogenated product which can be hydrolyzed into lysine.

COMPARATIVE EXAMPLE A

Example 1 is repeated but without addition of sodium hydroxide.

The sample taken before hydrogenation contains 5 mg of nickel per liter. After the hydrogenation, the nickel content measured in a sample of the reaction mixture was 1160 mg nickel/l, while 5-(3-cyanopropyl) hydantoin was no longer detected. A portion of the sample is hydrolyzed and its lysine content is determined. This test discloses that at least 88% of the cyano hydantoin has been converted into hydrogenated product which can be hydrolyzed into lysine.

COMPARATIVE EXAMPLE B

Example 1 is repeated, but with addition of much less sodium hydroxide, 12 g (representing 0.4 mole per mole of hydantoin) instead of 30 g.

The sample taken before hydrogenation contains 2 mg nickel/l. After hydrogenation, the nickel content of the reaction mixture equals 1170 mg/l, while 5-(3-cyanopropyl) hydantoin is not demonstrated anymore. A portion of the latter sample is hydrolyzed and its lysine content is determined. It appears that at least 88% of the cyano hydantoin has been converted into hydrogenated product which an be hydrolyzed into lysine.

COMPARATIVE EXAMPLE C

Example 1 is repeated, but with addition of much more sodium hydroxide, viz. 120 g (4 moles per mole of hydantoin) instead of 30 g.

A sample taken before hydrogenation contains 2 mg nickel per liter. After hydrogenation, the nickel content measured in a sample of the reaction mixture has decreased to 1 mg/l, while 5-(3-cyanopropyl) hydantoin is no longer evident.

A portion of the latter sample is hydrolyzed and its lysine content is determined. The test shows that only 34% of the cyano hydantoin has been converted into hydrogenated product which can be hydrolyzed into lysine.

EXAMPLE 2

Example 1 is repeated, but with the addition of potassium hydroxide (50g, a ratio of 1.2 mole per mole of hydantoin) instead of 30g sodium hydroxide. A sample taken before hydrogenation contains 1 mg nickel/l. After the reaction, the nickel content measured in a sample is still 1 mg/l, while 5-(3-cyanopropyl) hydantoin is no longer demonstrated.

A portion of the latter sample is hydrolyzed and its lysine content is determined. It appears that at least 88% of the cyano hydantoin has been converted into hydrogenated product which can be hydrolyzed into lysine.

EXAMPLE 3

Example 1 is repeated, starting, however, with a mixture of 5-(3-cyanopropyl) hydantoin (110g) and 16.5g of 2-ureido-5-cyanovaleramide in (1500 ml, 25% wt). A sample taken before hydrogenation contains 3 mg nickel/l.

After the reaction, another sample is taken in which 5 mg nickel/l, but none of the starting compounds, can be detected. A portion of the latter sample is hydrolyzed and its lysine content is determined. It appears that at least 89% of the starting products have been hydrogenated into products which can be hydrolyzed into lysine.

EXAMPLE 4

Example 1 is repeated, using, however, Raney cobalt (12.5g) instead of Raney nickel (12.5g). A sample taken before hydrogenation contains 5 mg cobalt/l. After the reaction another sample is taken, in which 6 mg of cobalt/l but no cyano hydantoin can be detected. A portion of the latter sample is hydrolyzed and its lysine content is determined. It is found that at least 88% of the starting product has been hydrogenated into product which can be hydrolyzed into lysine.

The above experiments are summarized in the following Table and demonstrate that an amount of dissolved alkali hydroxide in excess of 0.4 mole of the hydroxide per mole of compound to be hydrogenated are required to prevent the catalyst system from dissolving. On the other hand, too large an amount of dissolved alkali hydroxide maintains the catalyst but the selectivity of the reaction is lost.

| Ex. | Alkali hydroxide (Moles/Moles Cyan-Hydantoin) | Catalyst Content Reaction Mixture | Catalyst Content After Hydrogenation | Conversion |
|---|---|---|---|---|
| 1 | 1 NaOH | 3 | 7 | 87 |
| A | — | 5 | 1160 | 88 |
| B | 0,4 NaOH | 2 | 1170 | 88 |
| C | 4 NaOH | 2 | 1 | 34 |
| 2 | 1,2 KOH | 1 | 1 | 94 |
| 3 | 1 NaOH | 3 | 5 | 89 |
| 4 | 1 NaOH | 5 | 6 | 88 |

We claim:

1. In a process for preparing 5-(4-amino-butyl) hydantoin including hydrogenating 5-(3-cyanopropyl) hydantoin in the liquid phase in the presence of ammonia and a hydrogenation catalyst containing nickel, cobalt or both, the improvement wherein the hydrogenation is conducted in the presence of greater than 0.4 and not more than about 2.0 moles of a dissolved alkali hydroxide per mole of hydantoin to be hydrogenated.

2. The process according to claim 1 wherein from about 0.6 to about 1.5 moles of alkali hydroxide is used per mole of hydantoin.

3. In a process for preparing 5-(4-amino-butyl) hydantoin and 2-ureido-6-aminocapronamide including hydrogenating a mixture of 5-(3-cyanopropyl) hydantoin and 2-ureido-5-cyanovaleramide in the liquid phase in the presence of ammonia and a hydrogenation catalyst containing nickel, cobalt or both, the improvement wherein the hydrogenation is conducted in the presence of greater than 0.4 and not more than about 2.0 moles dissolved alkali hydroxide per mole of compound to be hydrogenated.

4. The process according to claim 3 wherein from about 0.6 to about 1.5 moles of alkali hydroxide is used per mole of hydantoin.

* * * * *